US009056315B2

(12) United States Patent
Xu

(10) Patent No.: US 9,056,315 B2
(45) Date of Patent: Jun. 16, 2015

(54) DUAL PHASE CATALYSTS SYSTEM FOR MIXED OLEFIN HYDRATIONS

(71) Applicant: Saudi Arabian Oil Company, Dhahran (SA)

(72) Inventor: Wei Xu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 14/490,148

(22) Filed: Sep. 18, 2014

(65) Prior Publication Data

US 2015/0005152 A1    Jan. 1, 2015

Related U.S. Application Data

(60) Division of application No. 14/025,318, filed on Sep. 12, 2013, now Pat. No. 8,865,951, and a continuation of application No. 12/946,014, filed on Nov. 15, 2010, now Pat. No. 8,558,036.

(51) Int. Cl.

| | |
|---|---|
| *B01J 29/04* | (2006.01) |
| *B01J 31/34* | (2006.01) |
| *C07C 29/04* | (2006.01) |
| *C07C 31/12* | (2006.01) |
| *C10L 1/02* | (2006.01) |
| *C10L 1/182* | (2006.01) |
| *B01J 31/08* | (2006.01) |
| *B01J 27/16* | (2006.01) |
| *B01J 27/18* | (2006.01) |
| *B01J 29/70* | (2006.01) |

(52) U.S. Cl.
CPC ............... *B01J 31/34* (2013.01); *C07C 29/04* (2013.01); *C07C 31/12* (2013.01); *C10L 1/02* (2013.01); *C10L 1/023* (2013.01); *C10L 1/026* (2013.01); *C10L 1/1824* (2013.01); *B01J 31/08* (2013.01); *B01J 27/16* (2013.01); *B01J 27/18* (2013.01); *B01J 29/70* (2013.01)

(58) Field of Classification Search
CPC ........... C07C 29/04; C07C 31/12; B01J 31/08
USPC .......................................... 502/60, 150, 208
See application file for complete search history.

(56) References Cited

U.S. PATENT DOCUMENTS

| | | | |
|---|---|---|---|
| 3,452,106 A | 6/1969 | Fukuzo Sato et al. | |
| 3,950,442 A | 4/1976 | Vogel et al. | |
| 3,994,983 A | 11/1976 | Webers et al. | |
| 4,011,271 A | 3/1977 | Gardner | |
| 4,011,272 A | 3/1977 | Matsuzawa et al. | |
| 4,038,211 A | 7/1977 | Frampton | |
| 4,065,512 A | 12/1977 | Cares | |
| 4,150,245 A | 4/1979 | Sommer et al. | |
| 4,154,580 A | 5/1979 | Landis | |
| 4,180,688 A | 12/1979 | Imaizumi et al. | |
| 4,182,920 A | 1/1980 | Giles et al. | |
| 4,214,107 A | 7/1980 | Chang et al. | |
| 4,234,748 A | 11/1980 | Frampton et al. | |
| 4,236,034 A | 11/1980 | Aoshima et al. | |
| 4,267,379 A | 5/1981 | Austin et al. | |
| 4,267,397 A | 5/1981 | Schmidt et al. | |
| 4,270,011 A | 5/1981 | Okumura et al. | |
| 4,284,831 A | 8/1981 | Okumura et al. | |
| 4,285,223 A | 8/1981 | Das et al. | |
| 4,307,257 A | 12/1981 | Sada et al. | |
| 4,339,617 A | 7/1982 | Imai et al. | |
| 4,351,970 A | 9/1982 | Sommer et al. | |
| 4,357,479 A | 11/1982 | Imai | |
| 4,358,626 A | 11/1982 | Okumura et al. | |
| 4,456,776 A | 6/1984 | Neier et al. | |
| 4,476,333 A | 10/1984 | Neier et al. | |
| 4,499,313 A | 2/1985 | Okumura et al. | |
| 4,579,984 A | 4/1986 | Neier et al. | |
| 4,652,544 A | 3/1987 | Okazaki et al. | |
| 4,783,555 A | 11/1988 | Atkins | |
| 4,831,197 A | 5/1989 | Henn et al. | |
| 4,861,923 A | 8/1989 | Olah | |
| 4,927,977 A * | 5/1990 | Child et al. | 568/695 |
| 4,954,660 A | 9/1990 | Messina et al. | |
| 4,982,022 A | 1/1991 | Smith, Jr. et al. | |
| 5,288,924 A | 2/1994 | Beech, Jr. et al. | |
| 5,349,096 A | 9/1994 | Cockman et al. | |
| 5,616,815 A | 4/1997 | Atkins | |
| 5,672,782 A | 9/1997 | Hattori et al. | |
| 5,684,216 A | 11/1997 | Haining | |
| 5,824,825 A | 10/1998 | Lansink-Rotgerink et al. | |
| 6,072,090 A | 6/2000 | Cockman et al. | |
| 6,111,148 A | 8/2000 | Ogawa et al. | |
| 6,953,867 B2 | 10/2005 | Cockman et al. | |
| 7,002,050 B2 | 2/2006 | Santiago Fernandez et al. | |
| 7,026,519 B2 | 4/2006 | Santiago Fernandez et al. | |

(Continued)

FOREIGN PATENT DOCUMENTS

| | | |
|---|---|---|
| CN | 1210847 A | 3/1999 |
| CN | 1299801 A | 6/2001 |
| CN | 1511815 A | 7/2004 |
| CN | 101289368 A | 10/2008 |
| CN | 101395110 A | 3/2009 |
| CN | 101395111 A | 3/2009 |
| CN | 101481296 A | 7/2009 |
| EP | 0010993 A1 | 5/1980 |
| EP | 0162362 A1 | 11/1985 |
| EP | 0323268 A2 | 7/1989 |

(Continued)

OTHER PUBLICATIONS

International Search Report and Written Opinion Issued in related PCT Patent Application No. PCT/US2011/060703; dated May 7, 2012; 8 pages.

PCT Notification of Transmittal of the International Preliminary Report on Patentability issued in related PCT Patent Application No. PCT/US2011/060703; dated Feb. 18, 2013; 14 pages.

*Primary Examiner* — Sudhakar Katakam
*Assistant Examiner* — Pancham Bakshi
(74) *Attorney, Agent, or Firm* — Bracewell & Giuliani LLP; Constance Gall Rhebergen

(57) ABSTRACT

The catalyst systems include a dual phase catalyst system that includes a water soluble acid catalyst and a solid acid catalyst.

6 Claims, No Drawings

(56) References Cited

U.S. PATENT DOCUMENTS

| | | |
|---|---|---|
| 7,115,787 B2 | 10/2006 | Reusch et al. |
| 7,148,387 B2 | 12/2006 | Takahashi et al. |
| 7,179,948 B2 | 2/2007 | Scholz et al. |
| 7,482,497 B2 | 1/2009 | Hassan et al. |
| 7,622,618 B2 | 11/2009 | Yanagawa et al. |
| 8,558,036 B2 | 10/2013 | Xu |
| 2009/0005613 A1 | 1/2009 | Hassan et al. |
| 2009/0136392 A1 | 5/2009 | Hassan et al. |
| 2009/0137850 A1 | 5/2009 | Yanagawa et al. |

FOREIGN PATENT DOCUMENTS

| | | | |
|---|---|---|---|
| EP | 1479665 | A1 | 11/2004 |
| EP | 1970363 | A1 | 9/2008 |
| GB | 408982 | | 4/1934 |
| GB | 415427 | | 8/1934 |
| GB | 646497 | | 11/1950 |
| GB | 706392 | | 3/1954 |
| GB | 727665 | | 4/1955 |
| GB | 930093 | | 7/1963 |
| GB | 996691 | | 6/1965 |
| GB | 996780 | | 6/1965 |
| GB | 1371905 | | 10/1974 |
| GB | 1374368 | | 11/1974 |
| GB | 1444645 | | 8/1976 |
| GB | 2024812 | | 1/1980 |
| GB | 1564223 | | 4/1980 |
| WO | 2008115242 | A1 | 9/2008 |

\* cited by examiner

DUAL PHASE CATALYSTS SYSTEM FOR MIXED OLEFIN HYDRATIONS

CROSS-REFERENCE TO RELATED PATENT APPLICATIONS

This application is a continuation of U.S. patent application Ser. No. 12/946,014, filed Nov. 15, 2010, now U.S. Pat. No. 8,558,036, and a divisional application of U.S. patent application Ser. No. 14/025,318, filed Sep. 12, 2013. For purposes of United States patent practice, this application incorporates the contents of the prior Applications by reference in their entirety.

BACKGROUND OF THE INVENTION

1. Field of the Invention

The present invention relates to processes for making alcohols from olefins using a dual phase catalyst system and related compositions.

2. Description of the Related Art

Internal combustion engines are commonly used on mobile platforms, in remote areas or in lawn and garden tools. There are various types of internal combustion engines. Spark type engines compress volatile fuels, such as gasoline, before ignition. Compression type engines take in air and compress it to generate the heat necessary to ignite the fuel, such as diesel.

Although hydrocarbon fuels are the dominant energy resource for such engines, alcohols, especially methanol and ethanol, have been used as fuels. In the 1970s, gasohol, a blend of mostly gasoline with some ethanol, was introduced during the Arab oil embargo. The primary alcohol fuel currently is ethanol. Ethanol is generally blended into gasoline in various quantities, normally at 10%, which typically results in a higher octane rating than regular gasoline. E-85 fuel contains 85% ethanol and 15% gasoline and M-85 has 85% methanol and 15% gasoline. Unfortunately, at that time, many of the elastomeric engine seals, hoses and gasket components were designed only for gasoline or diesel and deteriorated with the use of ethanol. Furthermore, the engines had to be equipped with fluorinated elastomers to run ethanol-based fuels.

Further limitations exist with respect to the use of grain-based fuels. For example, grain ethanol is expensive to produce. Furthermore, producing sufficient quantities of grain ethanol to satisfy the needs of the transportation industry is not practical because food crops and feed crops are and have been diverted into fuel. In addition, both methanol and ethanol have relatively low energy contents when compared to gasoline on a volumetric basis. Methanol contains about 50,000 Btu's/gallon and ethanol contains about 76,000 Btu's/gallon while gasoline contains about 113,000 Btu's/gal.

Long chain alcohols are often used together with amines/anilines as inhibitors to prevent metal corrosion and rubber/plastics swellings caused by the ethanol fuels. These long chain alcohols, such as dodecanol, can also be used as emulsifying agents. Mixed low cost methanol and ethanol were used together with long chain alcohols to form alcohol blended diesels or used as emulsifying diesel adjustors. However, long chain alcohols are relatively expensive to produce. The methanol-based and ethanol-based diesels also suffer from the drawback that they need other additives, such as long chain alcohols, alkyl esters and fatty acids to maintain a minimum Cetane number above 40 and to assure the diesel burns efficiently.

Some time ago, lead was added to gasoline to boost its octane rating, thereby improving the antiknock properties of gasoline. Lead is being eliminated in most countries from gasoline for environmental reasons. In response to the need to phase out lead, gasoline sold in the United States and many other countries was blended with up to 15% volumes of methyl-tertiary-butyl-ether (MTBE), an oxygenate, in order to raise the octane rating and to reduce environmentally harmful exhaust emissions. The industry is replacing MTBE with the use of fermented grain ethanol, but as discussed above, producing the necessary quantities of grain ethanol to replace MTBE is problematic in specific regions.

Another additive that has been used in fuels is Methylcyclopentadienyl Manganese Tricarbonyl (MMT). MMT has been a controversial gasoline additive for many years. MMT is able to increase octane but it increases emissions, which may have an adverse effect on health and exhaust catalytic conversion systems.

In lieu of these questionable additives, alcohols, such as butanols, can be used as combustible neat fuels or an oxygenate fuel additives or constituents in various types of fuels. When used as an oxygenate fuel, the BTU content is closer to the energy content of gasoline than many of the methanol or ethanol based fuels, as shown in Table 1.

TABLE 1

Properties of Butanols as compared to Gasoline

| Fuel | Energy Density | Air-Fuel Ratio | Specific Energy | Heat of Vaporization | RON | MON |
|---|---|---|---|---|---|---|
| Gasoline | 32 | 14.6 | 2.9 | 0.36 | 91-99 | 81-89 |
| Butanols | 29.2 | 11.1 | 3.3 | 0.43 | 96-110 | 78-99.5 |

Alcohols can be prepared from olefins. There are no particularly effective olefin hydration processes, however, in place to convert mixed olefins into alcohols, especially butenes into butanols.

Hydrations of butenes to butanols are commercially important reactions as the products find several important industrial applications. Butanols have been deemed as second generation fuel components after ethanol. These butanols can be used as solvents or chemical intermediates for the production of corresponding ketones, esters, ethers, etc.

Butanols produced through typical bio-routes are not efficient and would not produce enough quantity to meet the demanding needs of the butanol market. Hydration, which is normally an acid catalyzed reaction, can be used, but it is costly. Because organic butenes have very low solubility in water, relatively strong acids are often required to achieve the desired kinetics to convert the butenes to alcohols. Other processes used to produce butanols are also expensive. For example, petrochemical routes to produce mixed butanols by hydroformation and hydrogenation from propylene and carbon monoxide are costly.

A conventional commercial method of production of secondary butyl alcohol includes using a two step processes in which the n-butenes are reacted with excess sulfuric acid (80%) to form the corresponding sulfate which is hydrolysed to SBA as follow:

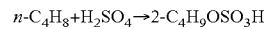

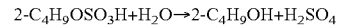

During this process, the sulfuric acid becomes diluted to about 35% concentration by weight and must be re-concentrated before it can be reused. The advantage of the process is its high conversion rate. However, many additional problems are usually associated when using such liquid catalysts. Among the problems are separation and recovery of the catalyst, corrosion of equipment and installations, and formation of byproducts such as secondary butyl ether, isopropyl alcohol, $C_5$-$C_8$ hydrocarbons, and polymers. Some of these byproducts complicate the purification of SBA.

Cationic exchange resins and zeolite are potentially important acid catalysts for olefin hydration. The cationic exchange resins are known to offer substantial rates in both polar and non-polar media. Attempts have been made to use sulfonated polystyrene resins cross linked with divinyl benzene as catalysts for the hydration of olefins such as propylene or butene. These types of catalyst systems offer several engineering benefits, such as ease in separation and provide a non-corrosive environment.

Butenes are sparingly soluble in water and form separated phases under the reaction conditions especially when butenes are used in a sufficiently large quantity. The butanol, being relatively non-polar, has a favorable distribution as a significant amount of butanols formed is expected to exist in the butene rich organic phase. Hence, simultaneous extraction during the course of the reactions might help in shifting the reversible reaction in the forward direction.

In spite of the currently available processes, there is no particularly effective route to produce mixed butanols through an economic route. Furthermore, the conversion rates of olefin hydration are low at less than 10% per pass.

A need exists for processes and systems that would allow for the direct catalytic hydration of alkenes to alcohols. It would also be beneficial if the processes and systems were inexpensive and provided a route to industrially useful alcohols and a convenient synthetic route for the synthesis of alcohols in general.

Additionally, there is a need for an additive or fuel that has improved octane rating as compared to gasoline and increased efficiency of combustion. There is a need for a fuel that reduces harmful emissions and airborne soot when combusted, either in neat form or as a fuel constituent.

There is also a need to provide a fuel of similar octane and BTU value to gasoline but without the use of tetraethyl lead, MTBE, methanol, ethanol, or MMT. It would also be desirable to provide a fuel additive that lowers the Reid Vapor Pressure of the fuel at least as well as, but without the use of, MTBE. It would be helpful if such fuels or additives would include mixed alcohols that are produced from mixed olefin streams.

SUMMARY OF THE INVENTION

In view of the foregoing, processes for producing alcohols from olefins and the catalyst systems for making such alcohols are provided as embodiments of the present invention. Additionally, processes for producing fuel compositions having alcohols prepared from olefins are also provided as embodiments of the present invention.

For example, as an embodiment of the present invention, a process for producing alcohols from olefins is provided. In this embodiment, a mixed olefin stream is contacted with a dual phase catalyst system to produce a mixed alcohol stream. The dual phase catalyst system includes a water soluble acid catalyst and a solid acid catalyst.

As another embodiment of the present invention, a process for producing a fuel composition from olefins is provided. In this embodiment, a mixed olefin stream is contacted with a dual phase catalyst system to produce a mixed alcohol stream. The dual phase catalyst system includes a water soluble acid catalyst and a solid acid catalyst. The mixed alcohol stream is then combined with a fuel component to produce the fuel composition. The fuel component of the fuel composition can be gasoline, diesel, jet fuel, aviation gasoline, heating oil, bunker oil, or combinations thereof.

Besides the process embodiments, a dual phase catalyst system for the production of mixed alcohols from mixed olefins is provided as an embodiment of the present invention. The dual phase catalyst system includes a water soluble acid catalyst and a solid acid catalyst.

DETAILED DESCRIPTION

Processes for producing alcohols from olefins and the catalyst systems for making such alcohols are provided as embodiments of the present invention. Additionally, processes for producing fuel compositions having alcohols prepared from olefins are also provided as embodiments of the present invention.

For example, as an embodiment of the present invention, a process for producing alcohols from olefins is provided. In this embodiment, a mixed olefin stream is contacted with a dual phase catalyst system to produce a mixed alcohol stream. The dual phase catalyst system includes a water soluble acid catalyst and a solid acid catalyst.

As used herein, "dual phase" catalyst system refers to a combination of two different types of acid catalysts that have been used individually to convert specific types of olefins into specific types of alcohols i.e., 2-butanol and t-butanol. Use of the term "dual phase" does not necessarily mean that two actual phases are present in the dual phase catalyst system. One of the catalysts in the dual phase catalyst system is soluble in water, while the other is not. The dual phase catalyst system of the present invention is capable of hydrating the mixed olefin stream without separating the olefins prior to contacting the mixed olefin stream with the dual phase catalyst system. The dual phase catalyst system is also capable of producing more than a single type or species of alcohol in the mixed alcohol stream. Thus, the resulting mixed alcohol stream contains a plurality of alcohol types.

As another embodiment of the present invention, a process for producing a fuel composition from olefins is provided. In this embodiment, a mixed olefin stream is contacted with a dual phase catalyst system to produce a mixed alcohol stream. The dual phase catalyst system includes a water soluble acid catalyst and a solid acid catalyst. The mixed alcohol stream is then combined with a fuel component to produce the fuel composition. The fuel component of the fuel composition can be gasoline, diesel, jet fuel, aviation gasoline, heating oil, bunker oil, or combinations thereof.

The catalyst system used in embodiments of the present invention includes two types of catalysts and is able to catalyze olefin hydration reactions with enhanced conversion rates. In such dual phase catalyst systems, olefins, such as butenes, propylene, LPG, reffinates of MTBE processes, or reffinates of TBA processes, are hydrated simultaneously with water to produce corresponding alcohols, such as secondary butyl alcohol (SBA), tertiary butyl alcohol (TBA), or isopropyl alcohol (IPA). An advantage of this dual phase catalyst system is that the olefin conversion rate of the olefin hydration reactions can increase up to 50% compared with single catalyst systems with the same residence time.

The source of the mixed olefin stream can vary. For example, in embodiments of the present invention, the mixed olefin stream is a discharge stream from a FCC unit, a thermal cracking unit, a reffinates stream from an MTBE process, a reffinates stream from a TBA process, a liquified petroleum gas (LPG) stream, or combinations thereof. Various types of olefins can be included in the mixed olefin stream. For example, in an aspect, the mixed olefin stream can include a mixed C4 stream. In an aspect, the mixed olefin stream can include propylene, n-butene, 2-butenes, isobutene, pentenes, hexenes, olefins having more than 6 carbons with at least two butenes, or combinations thereof. Other olefins that can be used in embodiments of the present invention include ethylene, propene, butenes, pentenes, or other higher olefins. Other suitable sources for the mixed olefin stream and types of olefins will be apparent to those of skill in the art and are to be considered within the scope of the present invention.

Most commercialized butene hydration processes are designed either with pure feeds, like 1-butene and iso-butene, or mixed feeds for selective iso-butene hydration. The process conditions are selected to maximize the yield of 2-butanol or yield of t-butanol within the limit of thermal dynamics. Because both 2-butanol and t-butanol are valuable oxygenates and octane enhancers for the fuels, embodiments of the present invention use an effective olefin hydration catalyst system to produce highly desired butanols, such as 2-butanol and t-butanol, for gasoline components from cheap mixed butenes.

Different butenes have different reaction rates under the same process conditions and catalyzed by the same catalyst. The present invention combines the advantages of both liquid acid catalyst and solid acidic catalyst to maximize the conversion rate of the mixed butene into mixed butanols.

Although the olefin hydration has been studied extensively, the main objective of the hydration is generally to produce one alcohol, not mixed alcohols as is produced by the methods and systems of the present invention, to avoid the complication of the separation of the alcohols. Because most alcohols are good fuel components, it is not necessary to separate them out. Therefore, a catalyst system that can convert all of the mixed olefins into alcohols, as in embodiments of the present invention, is highly desirable.

When the mixed alcohol stream primarily contains mixed butanols, the mixed alcohol stream produced in embodiments of the present invention can be referred to as "petro-butanols." The predominant butanols can be secondary butyl alcohol (SBA) and tertiary butyl alcohol (TBA) that can be obtained from mixed C4 olefin streams from an FCC unit or other thermal cracking units and reffinates of other processes, such as MTBE or TBA. As indicated herein, other suitable sources of olefin streams will be apparent to those of skill in the art and are to be considered within the scope of the present invention.

The processes described herein can occur in different types of equipment. For example, in an aspect, the step of contacting the mixed olefin stream can occur in a multi-staged reactor system. In another aspect, the step of contacting the mixed olefin stream can occur in a single reactor system. Other suitable types of process equipment that can be used in embodiments of the present invention will be apparent to those of skill in the art and are to be considered within the scope of the present invention.

Besides the process embodiments, a dual phase catalyst system for the production of mixed alcohols from mixed olefins is provided as an embodiment of the present invention. The dual phase catalyst system includes a water soluble acid catalyst and a solid acid catalyst.

The dual phase catalyst systems of the present invention can include a water soluble acid catalyst and a solid acid catalyst. In an aspect, the water soluble acid can include an organic acid, an inorganic acid, or combinations thereof. When the water soluble acid is an organic acid, the organic acid can be acetal acid, tosylate acid, perflurated acetic acid, lactic acid, citric acid, oxalic acid, benzoic acid, or combinations thereof. When the water soluble acid is an inorganic acid, the inorganic acid can be hydrochloric acid (HCl), phosphoric acid ($H_3PO_4$), sulfuric acid ($H_2SO_4$), hydrofluric acid, heteropoly acids, or combinations thereof. Particularly suitable water soluble acid catalysts include $H_3PO_4$ or $H_3[P(W3O10)4]xH_2O$. In an aspect, the solid acid catalyst can be an ionic exchange resin, a zeolite, a supported acid, or combinations thereof. An example of a suitable supported acid is phosphoric acid supported on silica. Particularly suitable acid catalysts are ionic exchange resins, such as Dowex® 50 resin from Dow Chemical Company, Amberlyst® 15 resin from Rohm and Haas, or D008 resin from KaiRui Chemical Co., Ltd., China. Optionally, phase transfer agents or surfactant catalysts can be added to aid in the olefin hydration reactions. Other suitable types of catalysts that can be used as the water soluble acid catalyst or the solid acid catalyst will be apparent to those of skill in the art and are to be considered within the scope of the present invention.

In an aspect, the water soluble acid catalyst and the solid acid catalyst are mixed together to form the dual phase catalyst system. The mixing of each component can occur prior to being added to the reactor or in the reactor. Other suitable methods for preparing the dual phase catalyst system, such as layering the components of the catalyst system, will be apparent to those of skill in the art and are to be considered within the scope of the present invention.

The amount of each catalyst can vary depending upon the mixed olefin stream being sent to the process. In an aspect, the weight ratio of the water soluble acid catalyst to the solid acid catalyst ranges from about 0.01 to about 100 in the dual phase catalyst system. In an aspect, the weight ratio of the water soluble acid catalyst to the solid acid catalyst is about 1:1. Other suitable amounts of each component of the dual phase catalyst system will be apparent to those of skill in the art and are to be considered within the scope of the present invention.

The dual phase catalyst system is more effective to convert mixed olefins into mixed alcohols than current commercialized single catalyst systems, such as (1) solution processes with sulfuric acid and (2) solid catalysts with ionic exchange resins. The dual catalyst system of the present invention is especially effective for the production of "petro-butanols", i.e. secondary butyl alcohol (SBA) and tertiary butyl alcohol (TBA) from mixed C4 olefin streams of FCC unit or other thermal cracking units and reffinates of other processes such as MTBE or TBA.

The processes and catalyst systems described herein can be used to produce various types of alcohols. For example, in an aspect, the mixed alcohol stream can include butanols. In another aspect, the mixed alcohol stream can include 2-butanol and t-butanol. The types of alcohols produced will depend upon the type of olefins contained in the mixed olefin stream and the types of catalyst selected. Other types of alcohol streams that can be produced using the processes and catalyst systems described herein will be apparent to those of skill in the art and are to be considered within the scope of the present invention.

The mixed alcohol stream made in accordance with embodiments of the present invention can be used as a component in fuel compositions or as a neat fuel composition. For example, in an aspect, a neat fuel composition is provided that includes a mixed butanol fuel having an octane rating suitable for use in combustion or compression engines. In another aspect, a fuel composition including a fuel component with a mixed butanol fuel is provided. In an aspect, the fuel component can include gasoline, diesel, jet fuel, aviation gasoline, heating oil, bunker oil, or combinations thereof. In an aspect, the mixed butanols can include n-butanol, 2-(+/−)-butanol, iso-butanol, tert-butanol, or combinations thereof; or alternatively, 2-(+/−)-butanol and tert-butanol. The mixed alcohol streams made in accordance with embodiments of the present invention can be used in other types of fuel compositions, as will be apparent to those of skill in the art and are to be considered within the scope of the present invention.

Using mixed alcohols, such as mixed butanols, as oxygenate fuel additives or constituents or as a neat fuel has several benefits. There are increased combustion efficiencies and reduced emissions of harmful gases and airborne soot. Other benefits of the mixed olefin fuels are that the BTU energy content is closer to the energy content of gasoline than that of methanol/ethanol based fuels. Butanols can be used as octane enhancers to replace tetra-ethyl-lead, MTBE, methanol, ethanol, MMT and other octane boosters without the negative environmental impacts. As another benefit, butanols have low and stable Reid Vapor Pressure blending characteristics and are much less corrosive than methanol/ethanol, which enables them to be used by existing storage and transportation facilities. Butanol based fuels can be used in existing engines without modifications. Furthermore, butanols are low toxicity components and normally readily biodegradable.

Another advantage of the dual phase catalyst system of the present invention is that the catalyst system is able to hydrate mixed olefin with higher conversion rates than commonly used commercial catalysts. The pre-separation of the olefins that is typically needed is not required. By using the methods and systems of the present invention, the whole fraction of olefins, such as butenes, can be utilized for the manufacture of useful gasoline additives. The lower RVP of the alcohols, such as butanols, will allow larger quantities of higher alkane, such as pentane, additions in gasoline.

A further advantage is that the whole products, particularly butanols, can be utilized as useful fuel components, oxygenates, and octane enhancers. The produced "petro-butanols" can be used as replacements of MTBE or ethanol in gasoline.

EXAMPLE

The following examples are given for the purpose of illustrating embodiments of the present invention. However, it is to be understood that these examples are merely illustrative in nature, and that the process embodiments of the present invention are not necessarily limited thereto.

All the pure butenes, inorganic acids, organic acids, ionic exchange resins, phase transfer agents and ionic liquids were purchased directly from the fine chemical supply market and used without any purification. Zeolites were synthesized according to published methods. The mixed butenes were obtained from one Saudi Arabia refinery without any other additives. The composition of the mixed butenes was determined by GC-MS and the concentrations were determined by GC method with detection limit at 3 ppm. The results are listed in Table 2.

TABLE 2

| Contents of the mixed butenes (wt. %) | | | | | | | | | | |
|---|---|---|---|---|---|---|---|---|---|---|
| C3= | C3 | C4= (total) | 2-t-C4= | 1-C4= | 2-c-C4= | i-C4= | i-C4 | n-C4 | i-C5 | n-C5 |
| 16.32 | 4.22 | 48.58 | 24.39 | 4.61 | 14.64 | 4.94 | 22.00 | 7.48 | 1.21 | 0.19 |

Butene Hydration

De-ionized water (200 g), a solid phase catalyst (6 g) selectively from zeolite in acid form, acidic ionic exchange resins, a water soluble acid selectively from $H_3PO_4$ and organic acids (6 g) and optionally phase transfer agent (Pr4NBr, 4 g) or/and hydration enhancers like copperic salts were all placed in a Parr autoclave. The autoclave was sealed and purged with $N_2$ at 50 psi for 10 times. Then, 10 mL of pure 2-trans-butene from AHG or 20 mL of mixed butenes from a Saudi Arabia refinery were charged to the autoclave under 50 psi of nitrogen gas. The mole ratio of water to butenes and the mole ratio of butenes to acid are listed in Table 3. The autoclave was then heated and maintained at a temperature of 150° C. there at for a period of 2-3 hours. At the end of this time, heating was discontinued; the autoclave was allowed to cool down to room temperature for 2 hours before the excess pressure was vented. The autoclave was then opened and the reaction mixture was recovered. The conversion rates and selectivity ratios were determined by means of gas chromatography. The conversion rates are listed in Table 3 with 100% selectivity to butanols unless otherwise indicated.

TABLE 3

| Hydration conditions and conversion rates | | | | | |
|---|---|---|---|---|---|
| Exp. No. | Catalyst | Mass (g) | 2-BuOH (ppm) | t-BuOH (ppm) | Conv. % | Selectivity ratio (2-OH/t-) |
| 1 | H3PO4, 2 g | 2 | 1092 | 1284 | 8.3 | 0.85 |
| 2 | Dowex 50WX8-H, 6 g | 6 | 2576 | 1287 | 13.3 | 2 |
| 3 | H3PO4, 2 g ' Dowex 50WX8-H, 6 g | 8 | 2778 | 1133 | 14.4 | 2.5 |
| Reaction Time of the set is 5 hrs. | | | | | | |
| 4 | H3PO4, 6 g | 6 | 1299 | 1223 | 8.9 | 1 |
| 5 | Amberlite 15, 6 g | 6 | 946 | 566 | 5.2 | 1.7 |

TABLE 3-continued

| | | | | | | |
|---|---|---|---|---|---|---|
| 6 | Amberlite 15, H3PO4, 6 g | 12 | 4065 | 1798 | 15.6 | 2.2 |
| 7 | H3[P(W3O10)4] × H2O, 6 g | 6 | 1109 | 1875 | 10.2 | 0.6 |
| 8 | Dowex 50WX8-H, 6 g | 6 | 2576 | 1287 | 13.3 | 2 |
| 9 | Dowex 50WX8-H, 6 g/ H3[P(W3O10)4] × H2O, 6 g | 12 | 3604 | 1234 | 16.5 | 2.9 |
| 10 | H3[P(W3O10)4] × H2O, 6 g | 6 | 1109 | 1875 | 10.2 | 0.6 |
| 11 | Amberlite 15, 6 g | 6 | 946 | 566 | 5.2 | 1.7 |
| 12 | Amberlite 15, 6 g/ H3[P(W3O10)4] × H2O, 6 g | 12 | 3057 | 1381 | 14.7 | 2.2 |
| 13 | Tungstosilicic acid hydrate, 6 g | 6 | 1414 | 1085 | 8.6 | 1.3 |
| 14 | Amberlite 15, 6 g | 6 | 946 | 566 | 5.2 | 1.7 |
| 15 | Amberlite 15, 6 g/ Tungstosilicic acid hydrate, 6 g | 12 | 2127 | 953 | 10.2 | 2.2 |

15 mL of Butenes, 200 g of water, 150° C., 200 psi and 3 hrs.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural references, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these reference contradict the statements made herein.

What is claimed is:

1. A dual phase catalyst system for the production of mixed alcohols from mixed olefins, the dual phase catalyst system comprising:
   a water soluble acid catalyst selected from phosphotungstic acid hydrate and tungstosilicic acid hydrate and a solid acid catalyst that is insoluble in water,
   where the dual phase catalyst system is capable of hydrating the mixed olefins without requiring separation of the mixed olefins prior to contacting the dual phase catalyst system, and
   where the dual phase catalyst system is capable of converting the mixed olefins into the mixed alcohols at a conversion rate that is greater than either the conversion rate of the water soluble acid catalyst or the conversion rate of the solid acid catalyst.

2. The system of claim 1 where the solid acid catalyst is selected from the group consisting of an ionic exchange resin, a zeolite, a supported acid, and combinations thereof.

3. The system of claim 1 where the mixed olefins are selected from the group consisting of propylene, n-butene, 2-butene, isobutene, pentenes, hexenes, olefins having more than 6 carbons, and combinations thereof.

4. The system of claim 1 where the conversion rate for the dual phase catalyst system is equal to or greater than about 10%.

5. The system of claim 1 where the dual phase catalyst system is capable of converting the mixed olefins into the mixed alcohols having a ratio of 2-butanol to t-butanol that is greater than either the ratio of 2-butanol to t-butanol of the water soluble acid catalyst or the ratio of 2-butanol to t-butanol of the solid acid catalyst, and where the mixed olefins comprise butenes.

6. The system of claim 5 where the ratio of 2-butanol to t-butanol for the dual phase catalyst system is equal to or greater than about 2.0.

* * * * *